US 6,543,056 B2

(12) United States Patent
Spiteri

(10) Patent No.: US 6,543,056 B2
(45) Date of Patent: Apr. 8, 2003

(54) SLEEP SHIELD

(76) Inventor: Antonio Spiteri, 699 Highlands Dr., Canton, MI (US) 48188

( * ) Notice: Subject to any disclaimer, the term of this patent is extended or adjusted under 35 U.S.C. 154(b) by 0 days.

(21) Appl. No.: 09/819,918

(22) Filed: Mar. 29, 2001

(65) Prior Publication Data

US 2002/0138891 A1 Oct. 3, 2002

(51) Int. Cl.[7] .................................................. A61F 9/00
(52) U.S. Cl. ............................................................. 2/15
(58) Field of Search .......................... 2/9, 15, 206, 11; 132/319; 600/27

(56) References Cited

U.S. PATENT DOCUMENTS

| | | | | |
|---|---|---|---|---|
| 1,924,315 A | * | 8/1933 | Hemphill et al. | 2/15 |
| 2,191,937 A | | 2/1940 | Low | 2/17 |
| 2,305,080 A | | 12/1942 | Hemphill | 2/15 |
| 2,342,840 A | * | 2/1944 | Cadous | 2/15 |
| 2,671,898 A | * | 3/1954 | Wade | 2/15 |
| 2,716,981 A | * | 9/1955 | More | 2/15 |
| 2,891,252 A | * | 6/1959 | Lazo | 2/15 |
| 2,946,133 A | * | 7/1960 | Williams | 2/15 |
| 4,635,625 A | | 1/1987 | Teeple | 2/163 |
| 4,649,908 A | * | 3/1987 | Ghaly | 128/132 |
| 4,790,031 A | | 12/1988 | Duerer | 2/15 |
| D302,167 S | | 7/1989 | Sherman | D16/107 |
| 4,908,878 A | | 3/1990 | Tarragano | 2/9 |
| D388,812 S | | 1/1998 | Miehe | D16/301 |
| D410,021 S | | 5/1999 | Heyman | D16/301 |
| 5,940,886 A | | 8/1999 | McCarthy | 2/206 |

* cited by examiner

Primary Examiner—John J. Calvert
Assistant Examiner—Katherine Moran

(57) ABSTRACT

A sleep shield adapted to exclude ambient light from the eyes of an adult wearer. The masking region which covers the eyes of the wearer and the portion of the forehead directly thereabove is provided at its midpoint on the lower edge thereof with an arcuate indentation to accommodate the nose bridge of the wearer. The sleep shield formed of inner layer of soft fabric and an outer layer of clear flexible plastic both cooperate in a narrow pocket-like receptacle to facilitate the insertion of various accessories.

9 Claims, 9 Drawing Sheets

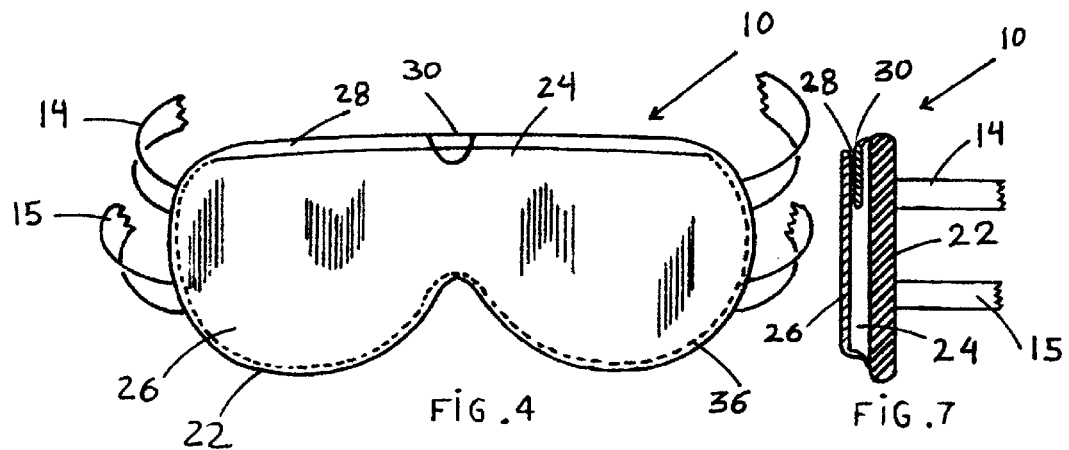
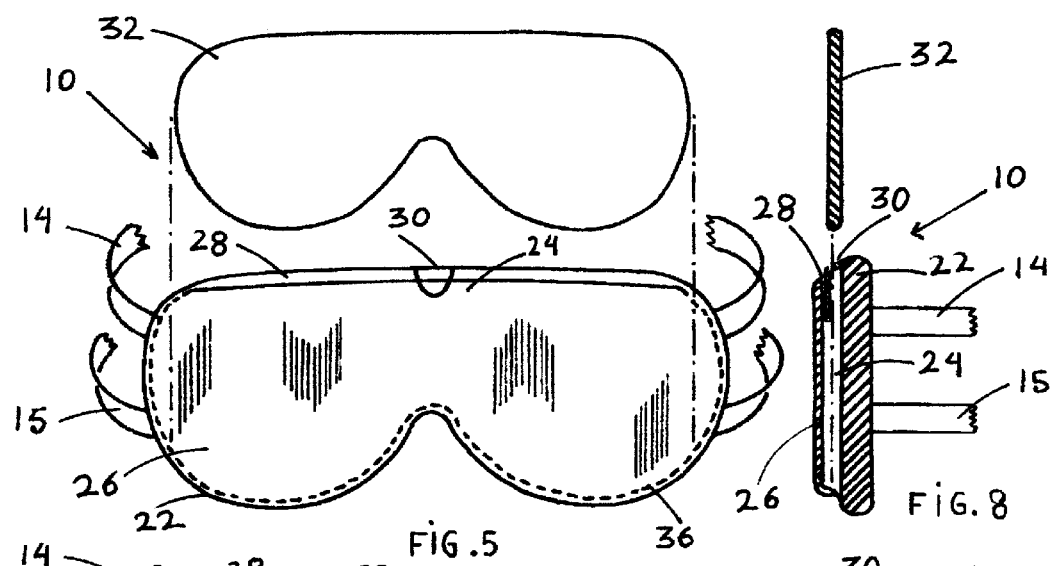
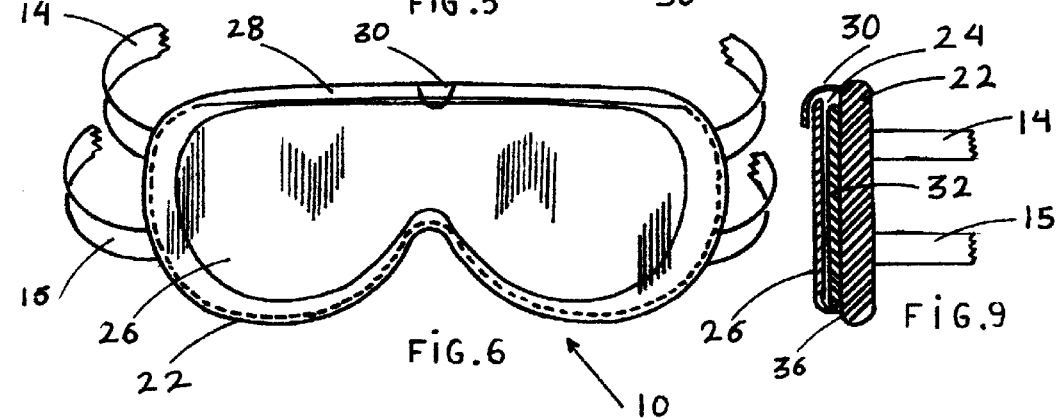

SLEEP SHIELD

BACKGROUND OF THE INVENTION

1. Field of Invention

This invention relates generally to sleep shades adapted to cover the wearer's eyes and having properties for inhibiting the passage of light throughout the shield to the eyes of the wearer.

2. Discussion of Prior Art

Adequate sleep is essential to well being, for without sleep one is deprived of the natural benefits that it provides. Yet the modern era has created an artificial environment for large segments of the population that demands to sleep under natural or artificial light. The human sensory system is not at idle during sleep, but stays alert to protect the sleeper. While the amount of ambient light striking on the eyes is vastly reduced when the eyelids are closed, nevertheless, the eyes remain responsive to ambient light. A common situation is that of a passenger of an airplane who has no choice but to sleep under lighted conditions.

Unfortunately, sleeping habits and state of minds vary, more so in a closed social crowd such as that of an airplane. Some travelers sleep with their sun-glasses worn so as not to be seen with their eyelids closed. It is also common prevention to sleep or to fall to a state of semi-consciousness to be afraid to miss a meal or a snack service. It is the human perception of these habits which often make them want to maintain some degree of consciousness. This of course interferes with the ultimate desire to sleep for a prolonged period of time.

SUMMARY OF THE INVENTION

In accordance with the present invention is to provide a sleep shield adapted to facilitate the sleep state of a wearer with ascetically appealing means to effectively exclude ambient light from the eyes of the wearer.

And more particularly, an object of this invention is to provide a sleep shield of the above type which is made of opaque layers of soft fabric forming a substrata unit and an outer layer of clear flexible plastic sheeting attached thereto, and cooperate in a fashion to allow the insertion, retention, displaying and withdrawal of graphic art. The resulting sleep shield inhibits the visual aspect of various sleeping habits by providing the sleep shield with a number of more appealing displays of the eye section of the face and more ascetically acceptable. Various graphic art accessories can also be provided for the sleep shield to otherwise facilitate the sleeping period of time. The shield can be attached to the head of the user using one or more ties, elastic bands, straps and buckles as well known in the art.

The graphic accessories or inserts can also be printed with indicia illustrating such as plain color, open or closed eyes, eyebrows, spectacles, sunglasses, gender, and race of the user, or simple statements such as "do no disturb" or "wake me for meal service." The resulting sleep should provide better peace of mind of the user thus enhancing every aspect of the sleeping period of item, resulting in a more relaxed sleep.

These and other features and advantages of the invention will become more apparent with a discussion of preferred embodiments in reference to the associated drawings.

BRIEF DESCRIPTION OF THE DRAWINGS

FIG. 4 is an elevation view of a sleep shield embodiment void of any insert configuration.

FIG. 5 is an elevation view of a sleep shield embodiment and a blank graphic art and its projected path inside the narrow housing receptacle.

FIG. 6 is an elevation view of a sleep shield embodiment with the insert adapted and secured inside the housing receptacle.

FIG. 7 is a cross section of a sleep shield shown in FIG. 4.

FIG. 8 is a cross section of a sleep shield shown in FIG. 5.

FIG. 9 is a cross section of a sleep shield shown in FIG. 6.

DETAILED DESCRIPTION OF THE DRAWINGS

Figure 1:
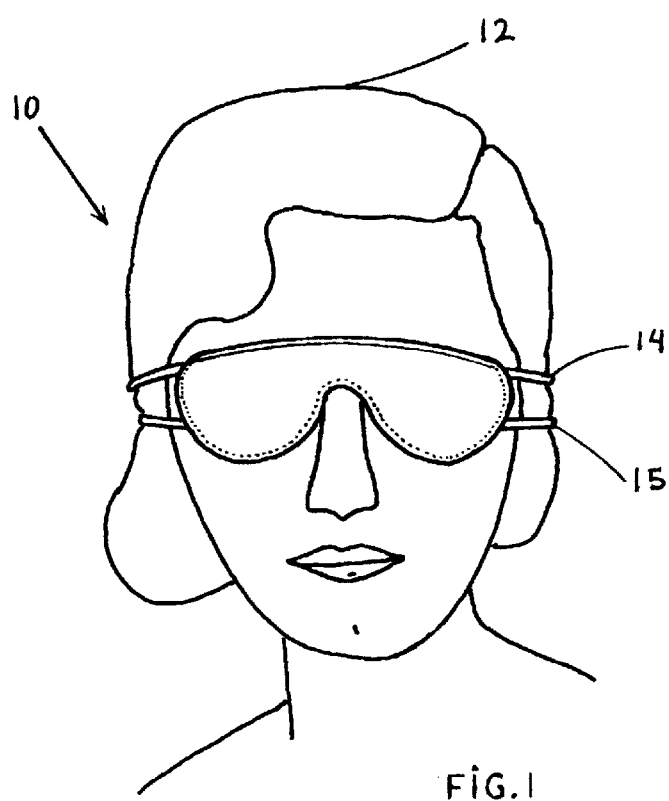
FIG. 1 is an elevation view of a sleep shield embodiment in position on a wearer.

Referring now to the drawings wherein like numerals have been used to indicate like elements in the several drawings.

A sleep shield as illustrated FIG. 1 and designated generally by the reference numeral 10, the sleep shield is shown to be operatively worn over the face of the wearer 12 in the shape and proportions to cover the area of an average size face. The eye shield includes sheets of soft, lightweight, and light-blocking fabric such as cotton and silk, forming the main body and the outermost sheet of clear flexible plastic, cooperates with the main body to form a narrow cavity to facilitate the insertion of mostly graphic art and plain color inlays. Elastic head straps 14 and 15 of continuous length are attached to the back inwardly side by means of stitching, symmetrically arranged in the upper and outer extremes of the main body element.

Figure 2:
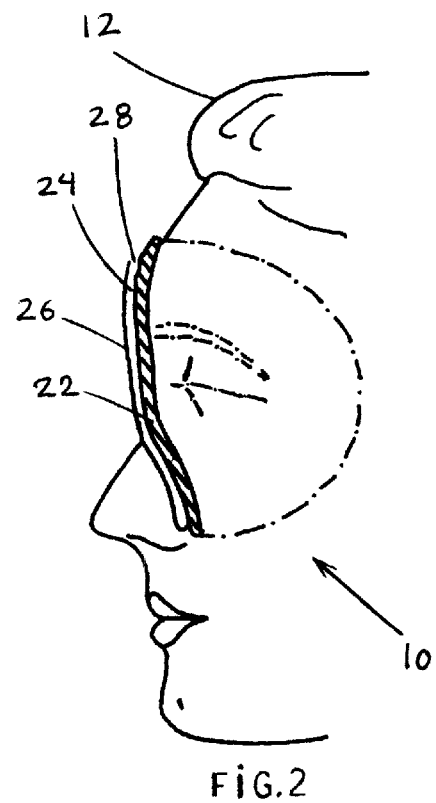
FIG. 2 is a cross-sectional view of a sleep shield shown in FIG. 1 with broken lines depicting, for illustrative purposes only, the extension covered by the shield.

FIG. 2 is a cross-sectional view of a sleep shield 10 shown in FIG. 1 illustrating the main body 22 fitted to the face of the wearer 12. An outermost layer made of clear flexible plastic 26 in juxtaposition to the main body sutured to the periphery so as to leave an opening 28 alongside the top portion of the shield 10 to form a narrow housing 24 to accommodate the insertion of graphic art inserts.

Figure 3:
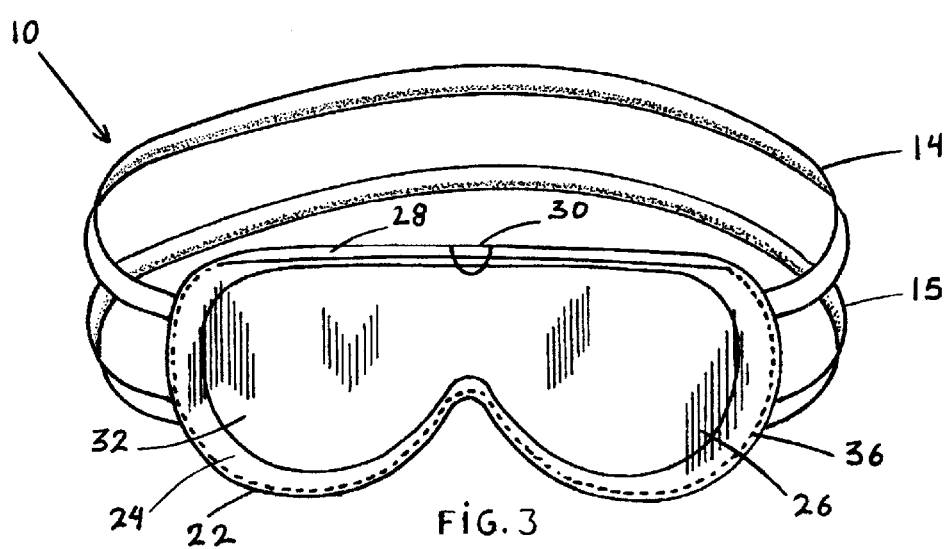
FIG. 3 is a perspective view of a light shield illustrating one embodiment carrying a blank insert arranged inside the narrow housing firmly secured therein by the small grasp retainer and a head strap configuration of particular advantage to the present invention.
Figure 10:
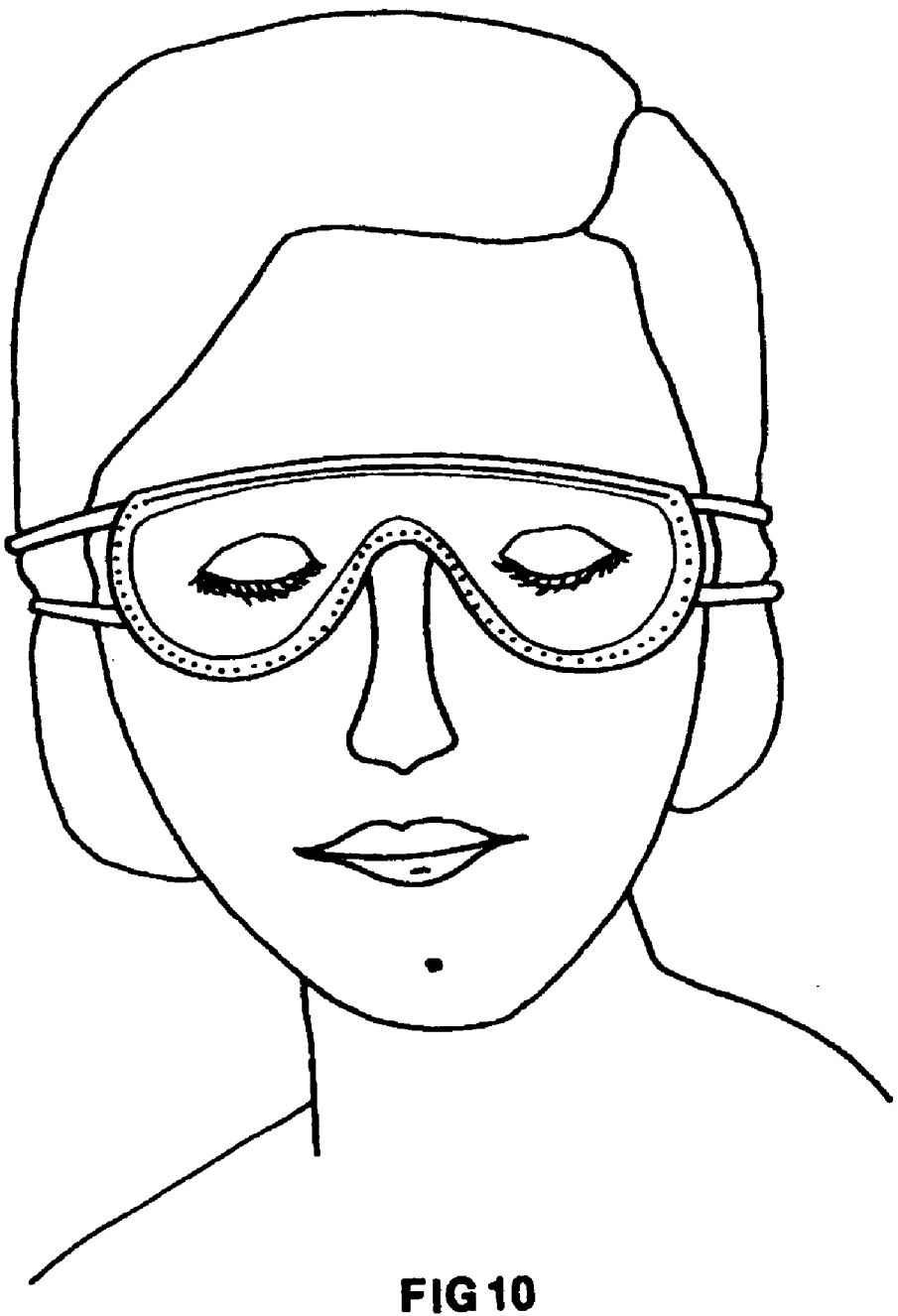
FIG. 10 is an elevation view of a sleep shield embodiment in position on a wearer depicting a pair of closed eyes and eyebrows.
Figure 11:
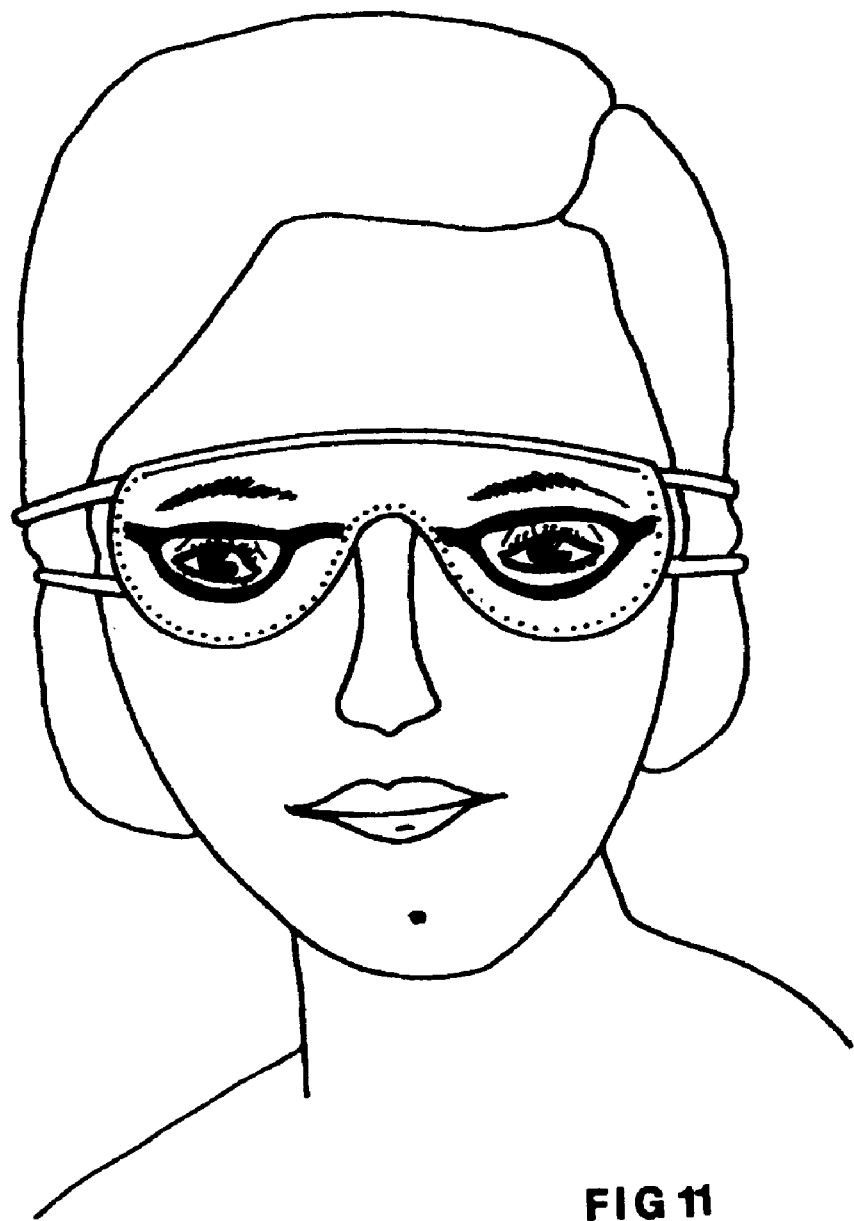
FIG. 11 is an elevation view of a sleep shield embodiment in position on a wearer depicting a pair of eyes with prescription lenses and eyebrows.
Figure 12:
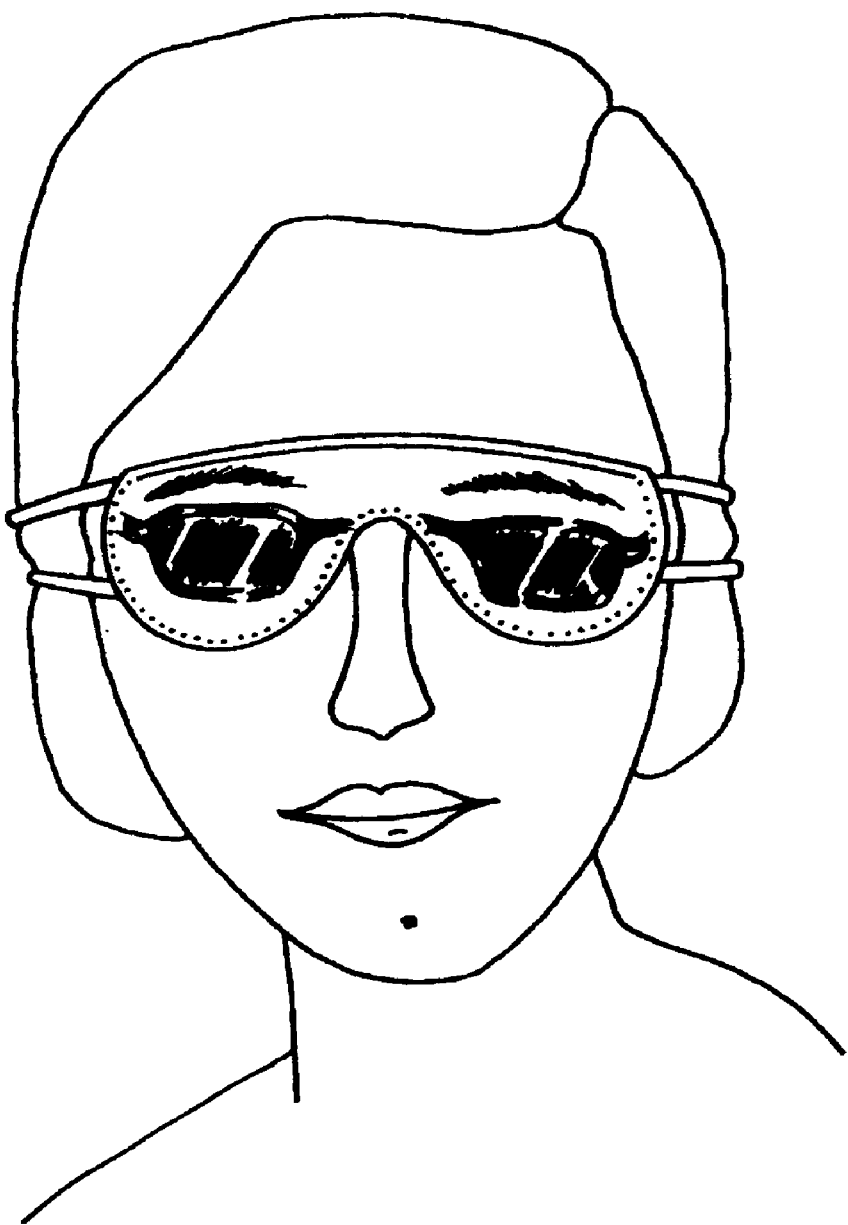
FIG. 12 is an elevation view of a sleep shield embodiment in position on a wearer depicting a pair of sunglasses and eyebrows.
Figure 13:
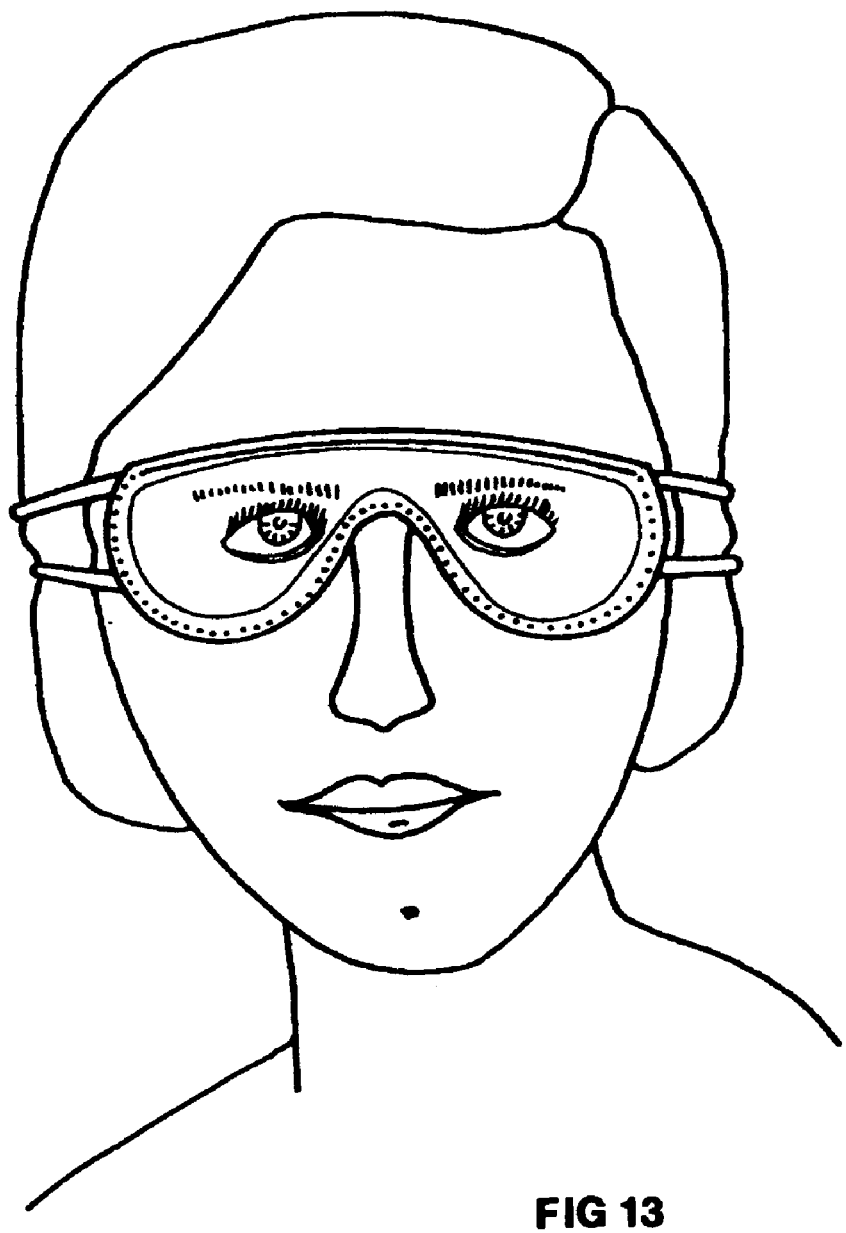
FIG. 13 is an elevation view of a sleep shield embodiment in position on a wearer depicting a pair of eyes open and eyebrows.
Figure 14:
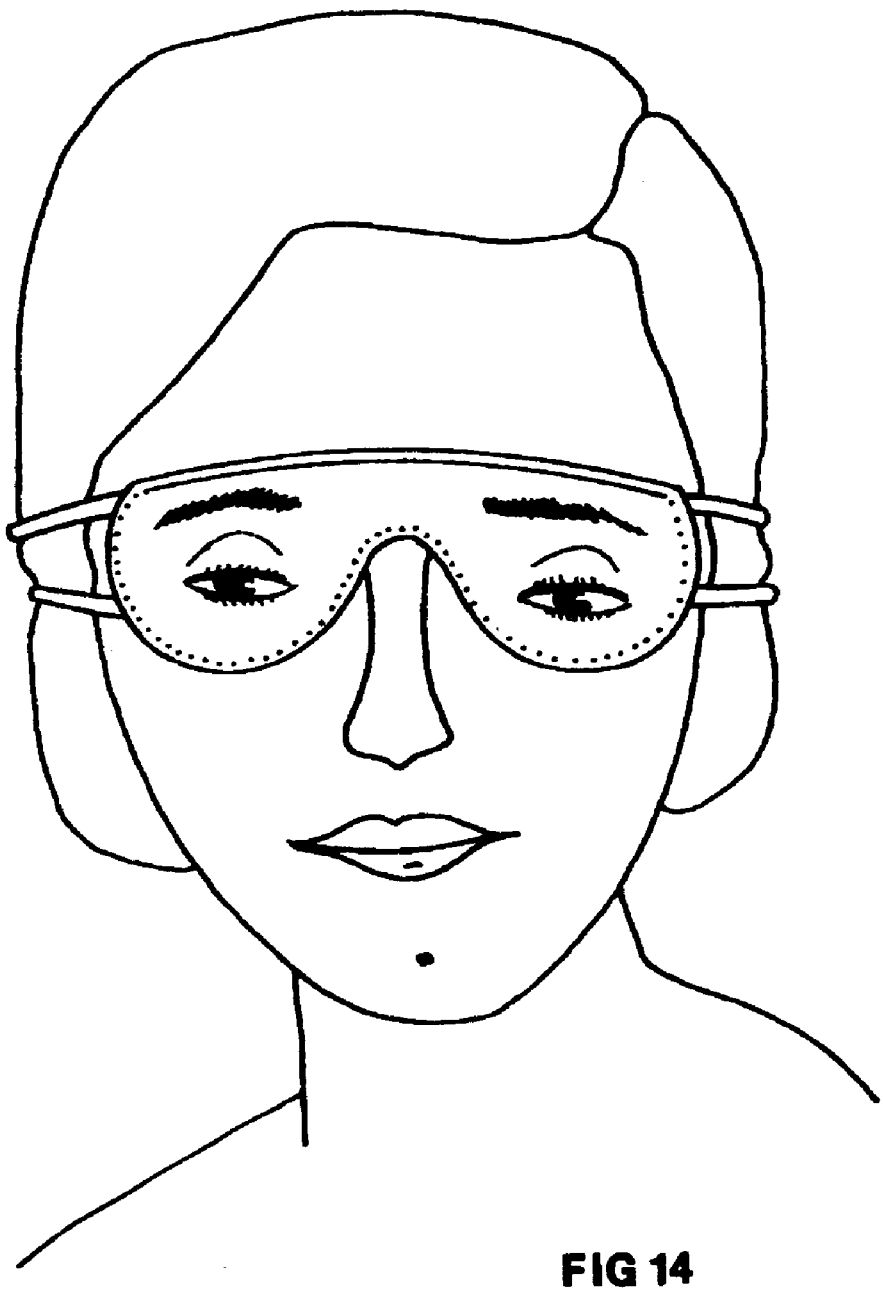
FIG. 14 is an elevation view of a sleep shield embodiment in position on a wearer depicting a pair of sleepy eyes and eyebrows.
Figure 15:
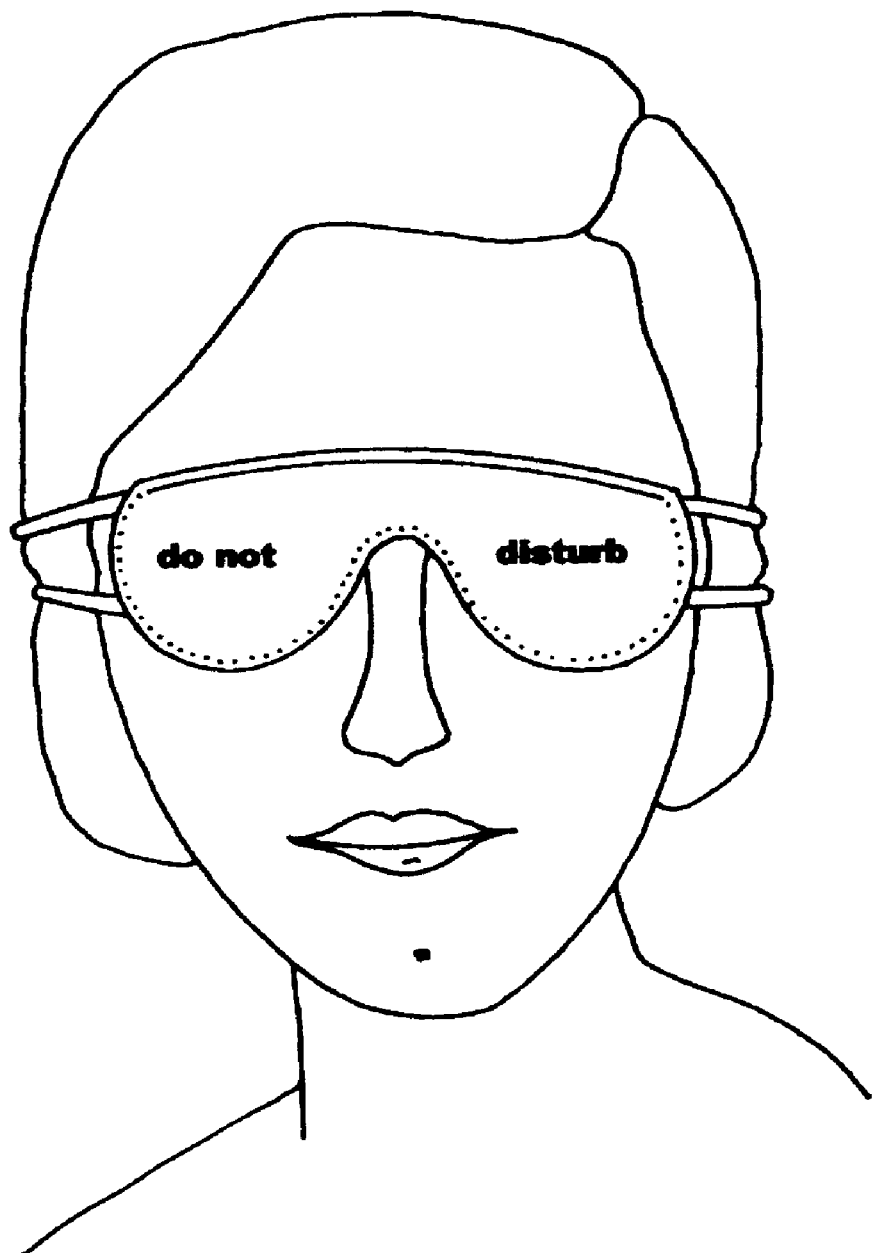
FIG. 15 is an elevation view of a sleep shield embodiment in position on a wearer depicting a short message.
Figure 16:
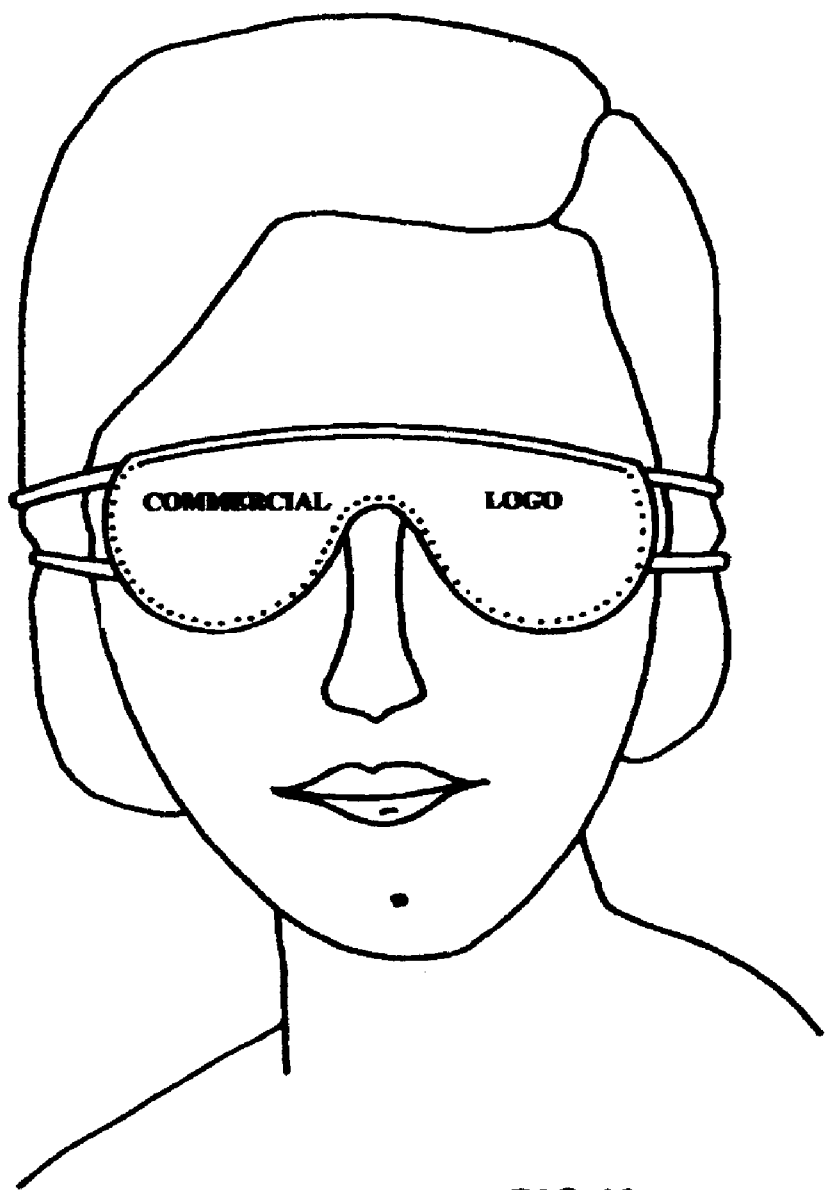
FIG. 16 is an elevation view of a sleep shield embodiment in position on a wearer depicting where a commercial logo can be printed.

A sleep shield 10, illustrated in greater detail in FIG. 3 will typically include a main body section 22 forming a seal with the face of the user 12 in order to inhibit the passage of light to the eyes of the person. This main body 22 will typically include one outermost layer of see-through flexible plastic 26 in juxtaposition and sutured thereof and is sized and configured to form a wide opening 28 to receive a number of mostly flat accessories 32 and retained inside the narrow housing 24 by means of a resilient grasp 30 in juxtaposition to said outer most see through plastic layer 26. A number of elastic head straps 14 and 15 of continuous length will hold aforementioned shield 10 gently fit to the face and head of the wearer 12.

A front view of the sleep shield 10 is illustrated in FIG. 4 where the narrow housing space 24 empty of any insert accessories 32 allowing the view of the main body 22 through the outermost layer of clear plastic 26 in juxtaposition and sutured thereof 36.

The embodiment of FIG. 5 illustrates the projected path of an insert 32 to slide through the narrow opening 28 to fit snugly inside the housing 24. To facilitate the sliding of said inserts 32 the wearer will previously gently stowed the grasp retainer 30 inside said cavity 24. Once the insertion process is terminated as the embodiment illustrated in FIG. 6. The user has also the option of bending forward said resilient grasp 30 juxtaposed to outermost layer of clear plastic 26 to prevent any further escape of any inserted material 32 by way of moving the head sideways against a pillow or other headrest. Alternatively, the wearer has also the choice not to employ said option since the inserts 32 are somewhat oversized to the width of the housing 28 thus restricting the unintentional ejection of any insert material 32 by way of moving the head during the sleep session.

In the foregoing embodiment of FIG. 7 displays a squematic cross section of sleep shield 10 as viewed on FIG. 4 with the resilient grasp 30 stowed inside the narrow housing 24. A further embodiment is shown in cross-section of FIG. 8 with the projected path sequence of an insert material 32 to be placed inside the narrow housing 24 by way of pressing gently said insert 32 to make way between outermost layer of see-through plastic 26 and resilient grasp 30. Another embodiment of FIG. 9 displays a schematic cross section of FIG. 6 with an insert material 32 stowed inside the narrow housing 24.

Giving these wide variations, which are all within the scope of this concept, one is cautioned not to restrict the invention to the embodiments which have been specifically disclosed and illustrated, but rather encouraged to determine the scope of the invention only with reference to the following claims:

I claim:

1. A sleep shield in combination with a graphic insert, adapted to facilitate sleep and convey a message for a wearer, said sleep shield comprising:

A soft, pliable, light blocking body element of a length and shape to extend across the wearer's face, including an upper portion adapted to rest against the wearer's forehead and a lowermost edge adapted to rest over the wearer's cheekbones;

A sheet of clear, flexible plastic material substantially affixed to the body element; thereby forming an inner cavity and opening in a top portion for receipt of a graphic insert;

A removable graphic insert positioned between the body element and plastic sheet;

A clear, resilient grasping means extending outwardly from the upper portion of the body element and adapted to overlie the plastic sheet in a closed position, for maintaining the graphic insert within the cavity; and Elastic retainer means extending from opposite sides of the body element, for maintaining the body against the wearer's face.

2. A sleep shield in combination with a graphic insert as in claim 1, wherein the insert displays a pair of closed eyes with eyebrows.

3. A sleep shield in combination with a graphic insert as in claim 1, wherein the insert displays a pair of eyes with prescription lenses and eyebrows.

4. A sleep shield in combination with a graphic insert as in claim 1, wherein the insert displays a pair of sunglasses with eyebrows.

5. A sleep shield in combination with a graphic insert as in claim 1, wherein the insert displays a pair of open eyes and eyebrows.

6. A sleep shield in combination with a graphic insert as in claim 1, wherein the insert displays a pair of semi-closed eyes and eyebrows.

7. A sleep shield in combination with a graphic insert as in claim 1, wherein the insert displays a short text message.

8. A sleep shield in combination with a graphic insert as in claim 1, wherein the insert displays a logo.

9. A sleep shield in combination with a graphic insert as in claim 1, wherein the insert displays a colored inlay.

\* \* \* \* \*